(12) United States Patent
Chumpolkulwong et al.

(10) Patent No.: US 8,603,774 B2
(45) Date of Patent: Dec. 10, 2013

(54) **EXTRACT OF *E. COLI* CELLS HAVING MUTATION IN RIBOSOMAL PROTEIN S12, AND METHOD FOR PRODUCING PROTEIN IN CELL-FREE SYSTEM USING THE EXTRACT**

(75) Inventors: Namtip Chumpolkulwong, Yokohama (JP); Chie Hori, Yokohama (JP); Shigeyuki Yokoyama, Yokohama (JP); Mikako Shirouzu, Yokohama (JP); Takanori Kigawa, Tsukuba (JP); Kozo Ochi, Tsukuba (JP); Takeshi Hosaka, Tsukuba (JP)

(73) Assignees: National Food Research Institute, Tsukuba-Shi (JP); Riken, Wako-Shi (JP)

( * ) Notice: Subject to any disclaimer, the term of this patent is extended or adjusted under 35 U.S.C. 154(b) by 314 days.

(21) Appl. No.: 11/137,395

(22) Filed: May 26, 2005

(65) Prior Publication Data

US 2006/0008871 A1    Jan. 12, 2006

Related U.S. Application Data

(63) Continuation of application No. PCT/JP03/15136, filed on Nov. 27, 2003.

(30) Foreign Application Priority Data

Nov. 28, 2002    (JP) ................................ 2002-345597

(51) Int. Cl.
  *C12P 21/02*    (2006.01)
(52) U.S. Cl.
  USPC ....................................... 435/68.1; 435/69.1

(58) Field of Classification Search
  USPC ................ 530/350; 435/69.1, 320.1, 252.3, 6
  See application file for complete search history.

(56) References Cited

U.S. PATENT DOCUMENTS

| 5,264,341 | A | 11/1993 | Maciak et al. |
| 5,270,181 | A | 12/1993 | McCoy et al. |
| 5,532,151 | A | 7/1996 | Chantry et al. |
| 5,674,729 | A | 10/1997 | Wimmer et al. |
| 5,800,984 | A | 9/1998 | Vary |
| 5,804,374 | A | 9/1998 | Baltimore et al. |
| 5,869,286 | A | 2/1999 | Yao et al. |

(Continued)

FOREIGN PATENT DOCUMENTS

| EP | 0469610 A1 | 2/1992 |
| EP | 1143009 A1 | 10/2001 |

(Continued)

OTHER PUBLICATIONS

Timms et al., Molecular and General Genetics, 1992, 232, 89-96.*

(Continued)

*Primary Examiner* — Rebecca Prouty
(74) *Attorney, Agent, or Firm* — Birch, Stewart, Kolasch & Birch, LLP

(57) ABSTRACT

It is intended to provide an extract, kit and a process for synthesizing a protein in a cell-free system. The extract is characterized by being prepared from mutant *Escherichia coli* cells having a mutation in the ribosomal protein S12 gene. In a preferred embodiment, the mutation is such a mutation as conferring a resistance or dependence to streptomycin on *E. coli* whereby the reading efficiency of mRNA codon on ribosomes can be improved and thus the protein productivity can be elevated.

4 Claims, 5 Drawing Sheets

(56) References Cited

U.S. PATENT DOCUMENTS

| | | | |
|---|---|---|---|
| 5,959,085 | A | 9/1999 | Garrone et al. |
| 5,962,246 | A | 10/1999 | Ladner et al. |
| 6,136,568 | A | 10/2000 | Hiatt et al. |
| 6,303,337 | B1 | 10/2001 | Rothschild et al. |
| 6,511,832 | B1 * | 1/2003 | Guarino et al. .............. 435/91.1 |
| 6,780,607 | B2 | 8/2004 | Choi et al. |
| 7,195,895 | B2 | 3/2007 | Motoda et al. |
| 7,348,134 | B2 | 3/2008 | Lingappa et al. |
| 2002/0025525 | A1 | 2/2002 | Shuber |
| 2002/0142387 | A1 | 10/2002 | Seki et al. |
| 2003/0050953 | A1 | 3/2003 | Sorge |
| 2004/0121346 | A1 | 6/2004 | Endo et al. |
| 2004/0137448 | A1 | 7/2004 | Thornton et al. |
| 2005/0095705 | A1 | 5/2005 | Kadan et al. |
| 2005/0244920 | A1 | 11/2005 | Shirouzu et al. |
| 2007/0281337 | A1 | 12/2007 | Imataka et al. |

FOREIGN PATENT DOCUMENTS

| | | |
|---|---|---|
| EP | 1 176 210 A1 | 1/2002 |
| EP | 1 316 616 A1 | 6/2003 |
| EP | 1354959 A1 | 10/2003 |
| EP | 1857558 A1 | 11/2007 |
| JP | 4-200390 A | 7/1992 |
| JP | 7-110236 A | 9/1995 |
| JP | 9-107954 A | 4/1997 |
| JP | 9-234074 A | 9/1997 |
| JP | 2000-175695 A | 6/2000 |
| JP | 2000-325076 A | 11/2000 |
| JP | 2002-238595 A | 8/2002 |
| JP | 2003-18999 A | 1/2003 |
| JP | 2003-235598 A | 8/2003 |
| JP | 2004-91790 A | 3/2004 |
| JP | 2004-215651 A | 8/2004 |
| JP | 2004-267205 A | 9/2004 |
| JP | 2004-290181 A | 10/2004 |
| JP | 2005-6646 A | 1/2005 |
| JP | 2005-225796 A | 8/2005 |
| WO | WO-88/08453 A1 | 11/1988 |
| WO | WO-92/07949 A1 | 5/1992 |
| WO | WO-92/11390 A1 | 7/1992 |
| WO | WO-92/13955 A1 | 8/1992 |
| WO | WO-97/46696 A1 | 12/1997 |
| WO | WO-99/02671 A1 | 1/1999 |
| WO | WO-99/14370 A1 | 3/1999 |
| WO | WO-99/20798 A1 | 4/1999 |
| WO | WO-99/57992 A1 | 11/1999 |
| WO | WO-00/56914 A1 | 9/2000 |
| WO | WO-01/83805 A2 | 11/2001 |
| WO | WO-02/18586 A1 | 3/2002 |
| WO | WO-02/90537 A1 | 11/2002 |
| WO | WO-03/097829 A1 | 11/2003 |

OTHER PUBLICATIONS

Funatsu et al., J. Mol. Biol., 68, 547-550, 1972.*
E. Kaltschmidt et al. "In Vitro Synthesis of Ribosomal Proteins Directed by *Escherichia coli* DNA", PNAS 71(2):446-450. (1974).*
J.L. Yates et al. "Effects of Ribosomal Mutations on the Read-Through of a Chain Termination Signal: Studies on the Synthesis of Bacteiophage λ O Gene Protein in vitro", PNAS 74(2): 689-693 (Feb. 1977).*
K Bohman et al. "Kinetic Impairment of Restrictive Streptomycin-Resistant Ribosomes", Mol. Gen. Genet. 198:90-99 (1984).*
Hwang, Y.-I., Database EMBL, Oct. 1, 2002, "Mutant 305 ribosomal subunit S12", XP-002353555.
Potapov A.P. et al., Biochimie, 1990, vol. 72, pp. 345 to 349.
Okamoto-Hosoya Y. et al., Microbiology, Nov. 2003, vol. 149, pp. 3299 to 3309.
Hu H. et al., Applied and Environmental Microbiology, Apr. 2001, vol. 67, pp. 1885 to 1892.
Hosoya Y. et al., Antimicrobial Agents and Chemotherap, Aug. 1998, vol. 42, pp. 2041 to 2047.
Chumpolkulwong, N. et al., Eur. J. Biochem. 2004, vol. 271, pp. 1127 to 1134.
Japanese Office Action for JP 2002-345597; issued Dec. 26, 2008.
Inaoka, Takashi et al., "Construction of an In Vivo Nonsense Readthrough Assay System and Functional Analysis of Ribosomal Proteins S12, S4, and S5 in *Bacillus subtilis*," Journal of Bacteriology, vol. 183, No. 17, pp. 4958-4963 (2001).
Giuliodori et al., "Preferential translation of cold-shock mRNAs during cold adaptation", RNA, vol. 10, pp. 265-276, 2004.
Nishimura et al., "Cell-Free System Derived from Heat-Shocked *Escherichia coil*: Synthesis of Enzyme Protein Possessing Higher Specific Activity", Journal of Fermentation and Bioengineering, vol. 79, No. 2, pp. 131-135, 1995.
Yu et al., 'An efficient recombination system for chromosome engineering in *Escherichia coli*', PNAS, vol. 97, No. 11, pp. 5978-5983, 2000.
Rowen et al., NCBI Protein AAF 02829, Submitted Apr. 25, 1999, Multimegabase Sequenceing Center, University of Washington.
Zubay, G., "In vitro synthesis of protein in microbial systems", Annual Review of Genetics, vol. 7, pp. 267-287, 1973.
Pratt et al., "Identification of gene products programmed by restriction endonuclease DNA fragments using an *E. coli* in vitro system", Nucleic Acids Research, Vol, 9, No. 18, pp. 4459-4474, 1981.
Benzinger et al., "Transfection of *Escherichia coil* Spheroplasts", Journal of Virology, vol. 15, No. 4, pp. 861-871, 1975.
Lorenz et al., "Bacterial Gene Transfer by Natural Genetic Transformation in the Environment", Microbiological Reviews, vol. 58, No. 3, pp. 563-602, 1994.
Yang et al., "Cell-free coupled transcription-translation system for investigation of linear DNA segments", Proc. Natl. Acad. Sol., vol. 77, No. 12, pp. 7029-7033, 1980.
Office Action mailed Sep. 14, 2010 in Japanese Application No. 2004-335514.
Wieder K. J. et al., Proceedings of the National Academy of Sciences of USA, 1982, vol. 79, pp. 3599-3603.
Abstract of Mikami S. et al., Protein Expression and Purification, Oct. 25, 2005.
Pain, Virginia M., et al., Analysis of Translational Activity of Extracts Derived from Oocytes and Eggs of Xenopus laevis, 1998, Methods in Molecular Biology, vol. 77, pp. 194-209, XP008075553.
Oilier et al., "A homologous in vitro system to analyze transcription of a mouse immunoglobulin u heavg-chain gene", Eur. J. Biochem., vol. 172, pp. 679-685, 1988.
Nishimura et al., "Enhancement of Protein Synthesis in Continuous-Flow, Cell-Free System by Improvement of Membrane Permeation", Journal of Fermentation and Bioengineering, vol. 80, No. 4, pp. 403-405, 1995.
Sigma-Aldrich product catalog page for Polyoxyethylene 23 lauryl ether (Brij 35), Dec. 15, 2004.
Bochkareva et al., "Chaperonin-promoted Post-translational Membrane Insertion of a Mullispanning Membrane Protein Lactose Permease", Journal of Biological Chemistry, vol. 271, No. 36, pp. 22256-22261, 1996.
Wheatley et al., "Glycosylation of G-protein-coupled receptors for hormones central to normal reproductive functioning: its occurrence and role", Human Reproduction Update, vol. 5, No. 4, pp. 356-364, 1999.
Kigawa et al., "Cell-free production and stable-isotope labeling of milligram quantities of proteins", FEBS Letters, vol. 442, pp. 15-19, 999.
Booth et al., Biochemical Society Transactions, vol. 28, Part 3, p. A50, 2000.
Kigawa et al., "High-throughput Cell-free Protein Expression System for Structural Proteomics", Protein, Nucleic Acid and Enzyme, vol. 47, No. 8, pp. 1014-1019, 2002.
Kain et al., "Universal Promoter for Gene Expression Without Cloning: Expression-PCR", BioTechniques, vol. 10, No. 3, pp. 366-368 and 370, 1991, XP000912135.
Macferrin et al., "Overproduction and dissection of proteins by the expression-cassette polymerase chain reaction", Proc. Natl. Acad. Sci., vol. 87, No. 5, pp. 1937-1941, 1990, XP000268593.
Ohuchi et al., "In vitro method for the generation of protein libraries using PCR amplification of a single DNA molecule and coupled

(56) References Cited

OTHER PUBLICATIONS transcription/translation", Nucleic Acids Research, vol. 26, No. 19, pp. 4339-4346, 1998, XP002119037.
Nakano et al., "Efficient Coupled Transcription/Translation from PCR Template by a Hollow-Fiber Membrane Bioreactor", Biotechnology and Bioengineering, Vol, 64, No. 2, pp. 194-199, XP001084028. 1999.
Ge et al., "Dual Asymmetric PCR: One-Step Construction of Synthetic Genes", BioTechniques, vol. 12, No. 1, pp. 14-16, 1992, XP002134139.
Horton et al., "Engineering hybrid genes without the use of restriction enzymes: gene splicing by overlap extension", Gene, vol. 77, pp. 61-68, 1989, XP002090392.
Liu et al., "Functional characterization of novel human ARFGAP3", FEBS Letters, vol. 490, Nos. 1-2, pp. 79-83, 2001.
Laage et al., "Strategies for Prokaryotic Expression of Eukaryotic Membrane Proteins", Traffic, vol. 2, No. 2, pp. 99-104, 2001.
Yoshida et al., "In Vitro Synthesis of Hyaluronan by a Single Protein Derived from Mouse HAS1 Gene and Characterization of Amino Acid Residues Essential for the Activity", Journal of Biological Chemistry, vol. 275, No. 1, pp. 497-506, 2000.
Lehto et al., "Release of the glycosylphosphatidylinositol-anchored enzyme ecto-5'-nucleotidase by phospholipase C: catalytic activation and modulation by the lipid bilayer", Biochem. Journal, vol. 332, pp. 101-109, 1998.
The pET Expression System, http://www.bio.davidson.edu/Course/Molbio?nolStudents/spring2003/Causey/p- ET.html, pp. 1-4, 2003.
Tucker et al., "Purification of a rat neurotensin receptor expressed in *Escherichia coil*", Biochem. Journal, vol. 317, pp. 891-899, 1996.
Grisshammer et al., "Expression of a rat neurotensin receptor in *Escherichia coli*", Biochem. Journal, vol. 295, pp. 571-576, 1993.
Abdulaev et al., "Functionally Discrete Mimics of Light-activated Rhodopsin Identified through Expression of Soluble Cytoplasmic Domains", Journal of Biological Chemistry, vol. 275, No. 50, pp. 39354-39363, 2000.
Sachdev et al., "Solubility of Proteins Isolated from Inclusion Bodies is Enhanced by Fusion to Maltose-Binding Protein or Thioredoxin", Protein Expression and Purification, vol. 12, No. 1, pp. 122-132, 1998.
Mcintyre et al., "Procathepsins L and D are Membrane-Bound in Acidic Microsomal Vesicles", Journal of Biological Chemistry, vol. 266, No. 23, pp. 15438-15445, 1991.
Invitrogen, "Flexible in vitro expression with high-yield results", Expressions, vol. 9, Issue 2, p. 7, 2002.
Novagen, "pET-23a-d(+) Vectors", p. 1, 1998.
Falk, "Cell-free synthesis and assembly of connexins into functional gap junction membrane channels", EMBO Journal, vol. 16, No. 10, pp. 2703-2716, 1997.
Rhee et al., "Channel-Forming Activity of Immunoaffinity-Purified Connexin32 in Single Phospholipid Membranes", Biochemistry, vol. 35, No. 28, pp. 9212-9223, 1996.
Ohtaki et al., "Expression, Purification, and Reconstitution of Receptor for Pituitary Adenylate Cyclase-activating Polypeptide", Journal of Biological Chemistry, vol. 273, No. 5, 15464-15473, 1998.
Mambetisaeva et al., "Expression of Three Functional Domains of Connexin 32 as Thioredoxin Fusion Proteins in *Escherichia coli* and Generation of Antibodies", Protein Expression and Purification, vol. 11, No. 1, pp. 26-34, 1997.
Peng et al., "Cystic fibrosis transmembrane conductance regulator: expression and helicity of a double membrane-spanning segment", FEBS Letters, vol. 413, No. 1, pp. 29-33, 1998.
Shehata et al., "Effect of Temperature on the Size of *Escherichia coil Cells*", Journal of Bacteriology, vol. 124, No. 2, pp. 857-862, 1975.
Patterson et al., "Deductive Analysis of a Protein-Synthesis Mutant of *Escherichia coli*", Biochemical Genetics, vol. 8, No. 2, pp. 205-230, 1973.
Klammt et al., "Cell-Free Production of Integral Membrane Proteins on a Preparative Scale", Methods in Molecular Biology, vol. 375, pp. 57-78, 2007.

Mathews et al., "Mammalian Cell-Free Protein Synthesis Directed by Viral Ribonucleic Acid", Eur. J. Biochem. vol. 17, pp. 328-338, 1970.
Zawada et al., "Effects of Genotype and Growth Conditions on Cell-Free Protein Synthesis Systems", Abstracts of Papers of the American Chemical Society, vol. 224, Nos. 1-2, p. BIOT 91, 2002, XP009068071.
Jones et al., "Function of a Relaxed-Like State following Temperature Downshifts in *Escherichia coil*", Journal of Bacteriology, vol. 174, No. 12, pp. 3903-3914, 1992.
Wang et al., "An Optimized Yeast Cell-Free System: Sufficient for Translation of Human Papillomavirus 58 L1 mRNA and Assembly of Virus-like Particles", Journal of Bioscience and Bioengineering, vol. 106, No. 1, pp. 8-15, 2008.
Hofbauer et al., "Preparation of a mRNA-Dependent Cell-Free Translation System from Whole Cells of *Saccharomyces cerevisiae*", Eur. J. Biochem, vol. 122, pp. 199-203, 1982.
Kim et al., "Expression-independent consumption of substrates in cell-free expression system from *Escherichia coil*", Journal of Biotechnology, vol. 84. pp. 27-32, 2000.
Kim et al., "Continuous Cell-Free Protein Synthesis Using Glycolytic Intermediates as Energy Sources", J. Microbiol. Biotechnol., vol. 18, No. 5, pp. 885-888, 2008.
Ertola et al., "Design, Formulation, and Optimization of Media", Bioprocess Technol., vol. 21, pp. 89-137, 1995.
Lee et al., "Statistical Medium Formulation and Process Modeling by Mixture Design of Experiment for Peptide Overexpression in Recombinant *Escherichia coil*", Applied Biochemist and Biotechnology, vol. 135, pp. 81-100, 2006.
Carroll et al., "Preparation of a Cell-Free Translation System with Minimal Loss of Initiation Factor eIF-2/eIF-2B Activity", Analytical Biochemistry, vol. 212, pp. 17-23, 1993.
Henis-Korenblit et al., "The caspase-cleaved DAP5 protein supports internal ribosome entry site-mediated translation of death proteins", PNAS, vol. 99, No. 8, pp. 5400-5405, 2002.
Person et al., "Translation in Micrococcal nuclease-treated cell-free extracts fromehrlich ascites tumor cells", Biochimica at Biophysica Acta., vol. 783, pp. 152-157, 1984.
Pestova et al., "The structure and function of initiation factors in eukaryotic protein synthesis", Cell. Mol, Life Sci., vol. 57, pp. 651-674, 2000.
Preiss et al., "Starting the protein synthesis machine: eukaryotic translation initiation", BioEssays, vol. 25, No. 12, pp. 1201-1211, 2003.
Thoma et al., "A Poly(A) Tail-Responsive in Vitro System for Cap- or IRES-Driven Translation from HeLa Cells", Methods in Molecular Biol., vol. 257, pp. 171-180, 2004, XP002496677.
Morley et al., "A rabbit reticulocyte factor which stimulates protein synthesis in several mammalian cell-free systems", Biochmica et Biophysica Acta, vol. 825, pp. 57-69, 1985.
Bergamini et al "Picornavirus IRESes and the poly(a) tail jointly promote cap-independent translation in a mammalian cell-free system", RNA, vol. 6, pp. 1781-1790, 2000.
Scheper et al., "Eukaryotic Initiation Factors-4E and -4F Stimulate 5' cap-dependent as Well as Internal Initiation of Protein Synthesis", Journal of Biological Chemistry, vol. 267, No. 11, pp. 7269-7274, 1992.
Scheper et al., "The 5' untranslated region of encephalomyocarditis virus contains a sequence for very efficient binding of eukaryotic initiation factor eIF-2/2B", Biochimica et Biophysica Acta, vol. 1089, pp. 220-226, 1991.
Nevins et al., "Distinct Regulation of Internal Ribosome Entry Site-mediated Translation following Cellular Stress is Medicated by Apoptotic Fragments of eIF4G Translation Initiation Factor Family Members eIF4G1 and p971DAP5/NAT1", Journal of Biological Chemistry, vol. 278, No. 6, pp. 3572-3579, 2003.
Imataka et al., "A newly identified N-terminal amino acid sequence of human eIF4G binds poly(A)-binding protein and functions in poly(A)-dependent translation", EMBO Journal, vol. 17, No. 24, pp. 7480-7489, 1998.
Svitkin et al., "Poly(A)-binding protein interaction with eIF4G stimulates picornavirus IRES-dependent dependent translation", RNA, vol. 7, pp. 1743-1752, 2001.

(56) References Cited

OTHER PUBLICATIONS

Imataka et al., "A new translational regulator with homology to eukaryotic translation initiation factor 4G", EMBO Journal, vol. 16, No. 4, pp. 817-825, 1997.

Mikami et al., "An efficient mammalian cell-free translation system supplemented with translation factors", Protein Expression and Purification, vol. 46, pp. 348-357, 2006.

Pelham et al., "An Efficient mRNA-Dependent Translation System from Reticulocyte Lysates", Eur. J. Biochem., vol. 67, pp. 247-256, 1976.

Lee et al., "Enhanced specific antibody productivity of calcium alginate-entrapped hybridoma is cell line-specific", Cytotechnology, vol. 16, pp. 1-15, 1994.

Sitaraman et al., "A novel cell-free protein synthesis system", Journal of Biotechnology, vol. 110, pp. 257-263, 2004.

Kim et al., "A highly efficient cell-free protein synthesis system from *Escherichia coil*", Eur. J. Biochem vol. 239, pp, 881-886, 1996.

Kigawa et al., "Preparation of Escherichia coli cell extract for highly productive cell-free protein expression", Journal of Structural and Functional Genomics, vol. 5, pp. 63-68, 2004.

Ha et al., "Immunostimulation with *Escherichia Coli* extract: prevention of recurrent urniary tract infections", International Journal of Antimicrobial Agents, vol. 31S, pp. S63-S67, 2008.

Hendrickson, W., "Determination of Macromolecular Structures from Anomalous Diffraction of Synchrotron Radiation", Science, Vol, 254, No. 5028, pp. 51-58, 1991.

Spirin et al., "A Continuous Cell-Free Translation System Capable of Producing Polypeplides in High Yield", Science, vol. 242, No. 4882, pp. 1162-1164, 1988.

Ge et al., "Simultaneous Introduction of Multiple Mutations Using Overlap Extension PCR", Biotechniques, vol. 22, No. 1, pp. 28 and 30, 1997.

Kigawa et al., "Cell-free synthesis and amino acid-selective stable isotope labeling of proteins for NMR analysis", Journal of Biomolecular NMR, vol. 6, No. 2, pp. 129-134, 1995.

Ikura M., "Heteronuclear 3D NMR and isotopic labeling of calmodulin. Towards the complete assignment of the 1H NRM spectrum", Biochem. Pharmacol., vol. 40, No. 1, pp. 153-160, 1990.

Patzlaff et al., "An isotope-edited FT-IR study of a symporter, the lactose permease", Biochem., vol. 41, pp. 7366-7372, 2002.

Ikura et al., "A novel approach for sequential assignement of 1H, 13C, and 15N spectra of proteins: heteronuclear triple resonance three-dimensional NMR spectroscopy, Application to calmodulin.", Biochemistry, vol. 29, pp. 4659-4667, 1990.

Weber et al., "Inhibition of Protein Synthesis by Cl", Journal of Biological Chemistry, vol. 252, No. 11, pp. 4007-4010, 1977.

Cooper et al., "Transcription of Vaccinia Virus mRNA Coupled to Translation In Vitro", Virology, vol. 88, No. 1, pp. 149-165, 1978.

Dougherty et al., "Translation of Potyvirus RNA in a Rabbit Reticulocyte Lysate: Reaction Conditions and Identification of capsid Protein as One of the Products of in Vitro Translation of Tobacco Etch and Pepper Mottle Viral RNAs", Virology, vol. 101, No. 2, pp. 466-474, 1980.

Hardwick et al., "Cell-free protein synthesis by kidney from the aging female fischer F344 rat", Biochimica et Biophysica Acta, vol. 652, No. 1, pp. 204-217, 1981.

Mori et al., "Cell-free translation of carbamyl phosphate synthetase I and ornithine transcarbamylase messenger RNAs of rat liver. Effect of dietary protein and fasting of translatable mRNA levels", Journal of Biological Chemistry, vol. 256, No. 8, pp. 4127-4132, 1981.

Cosgrove et al., "Absence of age differences in protein synthesis by rat brain, measured with an initiating cell-free system", Neurobiology of Aging, Vol, 8, No. 1, pp. 27-34, 1987.

Office Action mailed Aug. 10, 2010 in Japanese Application No. 2004-333250.

Bulleid et al., "Cell-free synthesis of enzymically active tissue-type plasminogen activator", Biochem. J., vol. 286 (Part 1), pp. 275-280, 1992.

Emmerich et al., "Characterisation of Protein Synthesis in Cell-Free Extracts from Different Mammalian Cells by their Sensitivity to Inhibitors of Polypeptide-Chain Initiation", Hoppe-Seyler's Z. Physiol. Chem., vol. 360, No. 8, pp. 1099-1111, 1979.

Evdokimova et al., "The major mRNA-associated protein YB-1 is a potent 5' cap-dependent mRNA stabilizer", The EMBO Journal, vol. 20, No. 19, pp. 5491-5502, 2001.

Ishifiara et al., "Expression of G protein coupled receptors in a cell-free translational system using detergents and thioredoxin-fusion vectors", Protein Expression and Purification, vol. 41, pp. 27-37, 2005.

Kalmbach et al., "Functional Cell-free Synthesis of a Seven Helix Membrane Protein: In situ Insertion of a Bacteriorhodopsin into Liposomes", J. Mol. Biol., vol. 371, pp. 639-648, 2007.

Kodukula et al., "Biosynthesis of phosphatidylinositol-glycan (PI-G)-anchored membrane proteins in cell-free systems: PI-G is an obligatory cosubstrate for COOH-terminal processing of nascent proteins", Proc. Natl. Acad. Sci., vol. 89, No. 11, pp. 4982-4985, 1992.

Merola et al., "Folding of hepatitis C virus E1 glycoprotein in a cell-free system", Journal of Virology, vol. 75, No. 22, pp. 11205-11217, 2001.

Walter et al., Preparation of Microsomal Membranes for Cotranslation Protein Translocation, Methods in Enzymology, vol. 96, pp. 87-93, 1983.

Svitkin et al., "Complete transition of the hepatitis C virus genome in vitro: membranes play a critical role in the maturation of all virus proteins except for NS3", Journal of Virology, vol. 79, No. 11, pp. 6868-6881, 2005.

\* cited by examiner

EXTRACT OF E. COLI CELLS HAVING MUTATION IN RIBOSOMAL PROTEIN S12, AND METHOD FOR PRODUCING PROTEIN IN CELL-FREE SYSTEM USING THE EXTRACT

This application is a Continuation of PCT/JP2003/015136 filed Nov. 27, 2003, which also claims priority to JP Patent Application No. 2002-345597. The entire contents of these applications are incorporated by reference.

TECHNICAL FIELD

The present invention relates to an extract prepared from mutant E. coli cells having a mutation in the ribosomal protein S12 gene, and to a method for producing a protein in a cell-free system using the extract.

BACKGROUND ART

A cell-free protein synthesis system using a cell extract is utilized mainly for identification of gene products and for investigation of their activities. For example, the system enables the analysis of functions of synthesized proteins such as the enzymatic activity and DNA binding capability, or the determination of the molecular weight of translated products by labeling them with radioisotopes. Recently, techniques of drastically increasing the production amount in the system have been developed, and the system has become utilized also for protein structure analysis through X-ray crystallography, NMR and the like.

For extracts to perform the translation reaction, those derived from E. coli, wheat germ, and rabbit reticulocyte are commercially available. For an E. coli extract, S-30 cell-free extract reported by Zubay et al. (e.g., see Non-Patent Reference 1) is commonly used. For preparing the E. coli S-30 extract, RNase I-defective strains such as A19 and D10 are used. However, when the target protein is sensitive to proteolytic degradation, E. coli strain B, which is defective in ompT endoprotease and lon protease activities may be used.

For synthesizing mRNA from a cloned cDNA, the cDNA must be introduced into a suitable vector having various promoters. For increasing the protein expression efficiency, intensive promoters for phage-derived polymerases such as T7, T3, and SP6 are used at present, and various systems suitable to various types of template DNAs are commercially available. Using such cell-free systems enables cloned DNA expression in an extremely simplified manner and enables cytotoxic protein synthesis.

However, it is known that systematic and comprehensive expression of a large number of genes obtained from the recent genome analysis results in the existence of genes of relatively low expression and genes of no expression. It is believed that the low expression of genes may be caused by the reduced efficiency in the translation stage based on the difference in the nucleotide sequence as compared with the genes of higher expression.

On the other hand, it is known that antibiotics-resistant actinomycetes strains have a property of enhanced producibility of secondary metabolites (antibiotics, etc.), and it is reported that these are derived from the point mutation of ribosomal protein genes. It is suggested that, in these mutants, the conformation of the 16S ribosomal RNA (hereinafter referred to as "16SrRNA") might change due to the point mutations of the ribosomal protein S12 and S4, which influence the mRNA reading efficiency (e.g., see Non-Patent Reference 2), but the mechanism, by which the mutation of the ribosomal protein enhances the production yield of the secondary metabolites of actinomycetes, is not yet clarified. It is reported that actinomycetes resistant to streptomycin, gentamycin and rifampicin have a property to express an extremely increased amount of a specific transcriptional regulatory protein in the growth stage (e.g., see Non-Patent Reference 3, FIG. 5). However, nothing has been clarified as yet, relating to the exogenous protein producibility in the extract of such actinomycetes cells. As compared with other bacteria, the growth speed of actinomycetes is slow and the optimum cultivation temperature thereof is low, and thus, it is difficult to provide a large quantity of cell extract of actinomycetes.

[Non-Patent Reference 1]
Geoffrey Zubay, Annual Review of Genetics, 1973, Vol. 7, pp. 267-287.
[Non-Patent Reference 2]
Yoshiko Hosoya & 3 others, Antimicrobial Agents and Chemotherapy, 1988, Vol. 42, pp. 2041-2047.
[Non-Patent Reference 3]
Haifeng Hu & 1 other, Applied and Environmental Microbiology, 2001, Vol. 67, pp. 1885-1892.

DISCLOSURE OF THE INVENTION

Therefore, it is an object of the present invention to increase the protein producibility by improving the codon reading efficiency of mRNA on ribosome in a cell-free protein synthesis system using an E. coli cell extract.

We, the present inventors, have studied the culture characteristics of streptomycin-resistant E. coli strains and the protein synthesis activity of the extract thereof, and, as a result, have found that the cell extract prepared from E. coli having a mutation in a specific site of the ribosomal protein S12 has an extremely high protein synthesis activity. On the basis of this finding, we have completed the present invention.

According to a first aspect of the present invention, there is provided a cell extract prepared from E. coli having a mutation in the ribosomal protein S12 gene.

In a preferred embodiment of this aspect of the invention, the mutation confers a resistance or dependence to streptomycin on E. coli. More preferably, the mutation causes an amino acid substitution in the ribosomal protein S12, and the amino acid substitution is at position 43 of the amino acid sequence represented in SEQ ID NO:2. Even more preferably, the amino acid substitution is a substitution from lysine to threonine. Owing to the ribosomal protein S12 having the amino acid substitution, the mutant strain can grow even in the presence of streptomycin and its cell extract exhibits high protein synthesis activity.

In another aspect of the present invention, there is provided a kit for cell-free protein synthesis, which comprises an extract for cell-free protein synthesis prepared from E. coli having a mutation in the ribosomal protein S12 gene, and a mixture comprising an energy regenerating system, at least one amino acid, nucleotide triphosphate, and/or an RNA polymerase. The mixture may be mixed with the E. coli extract just before the protein synthesis reaction, but may be previously mixed with it. Accordingly, in still another aspect thereof, the invention provides a mixture for cell-free protein synthesis, which comprises an extract for cell-free protein synthesis prepared from the above-mentioned E. coli, and at least one selected from the group consisting of an energy regenerating system, at least one amino acid, nucleotide triphosphate, and an RNA polymerase.

In still another aspect thereof, the invention further provides a process for producing a protein in a cell-free system. The process comprises preparing a polynucleotide that encodes a protein, and expressing the polynucleotide by the use of the extract for cell-free protein synthesis that is prepared from *E. coli* having a mutation in the ribosomal protein S12 gene. In some case for expressing a desired polynucleotide, the expression efficiency may be sometimes extremely low depending on the nucleotide sequence of the target polynucleotide, for example, due to any problems of the codon-anticodon pairing on the ribosome. The process of the invention solves the problem by introducing a specific mutation into the ribosomal protein S12, and results in an improvement of the expression efficiency of the polynucleotide that is resistant to express.

BEST MODE FOR CARRYING OUT THE INVENTION

Figure 1:
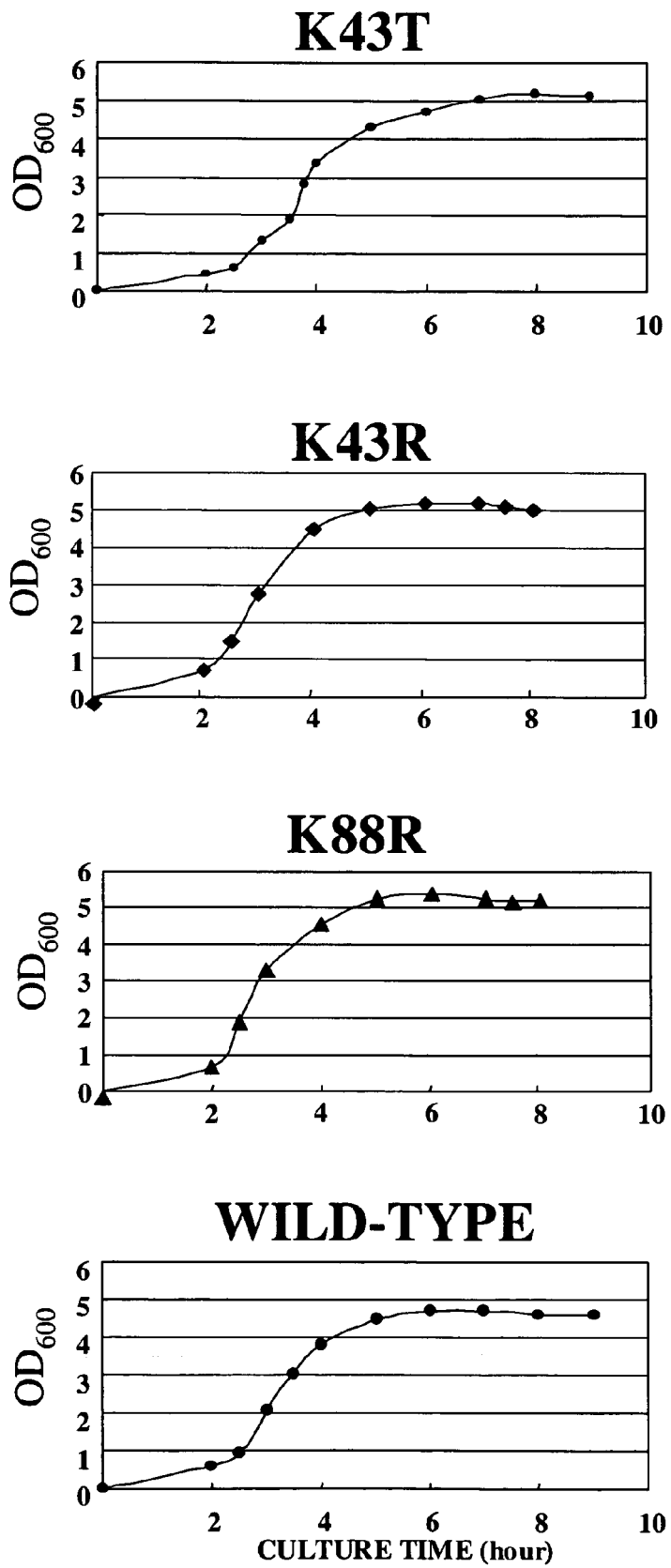
FIG. 1 shows growth curves of wild-type *E. coli* and *E. coli* having a mutation in the ribosomal protein S12, in terms of the culture turbidity ($OD_{600}$) relative to the culture time. All strains were cultivated in 2×YT medium at 37° C.

Preferred embodiments of the invention are described hereinunder with reference to the drawings.
(Ribosomal Proteins S12 Mutants, and their Antibiotic Resistance Mechanism)

The extract of *E. coli* cells of the invention is prepared by cultivating a mutant *E. coli* strains having a mutation in the ribosomal protein S12 and extracting the mutant cells. The ribosomal protein S12 is a type of ribosome-constitutive protein. It is known that, in *E. coli*, the ribosomal protein S12 binds with 16SrRNA to form a small subunit. For example, the amino acid sequence of protein S12 that constitutes the ribosome 30S of *E. coli* is registered in Acc. No. P02367 in SWISS-PROT, and the amino acid sequence is shown in SEQ ID NO:2.

A large complex comprising protein and RNA, that is, ribosome catalyzes various processes in the stage of protein translation. The structure and the function of the ribosome are very similar in both prokaryotes and eukaryotes, and pairs of small subunits gather to form a complex of millions of Daltons. The small subunit controls the binding of mRNA and tRNA, and the large subunit catalyzes the formation of peptide bond.

The elongation of polypeptide chain on ribosome includes binding of an aminoacyl tRNA to the site A on ribosome thereby causing base pairing with three nucleotides of the mRNA having appeared in that site. Next, the carboxyl terminal of the polypeptide chain binding to the tRNA molecule at the site P adjacent to the site A is left away, and a peptide bond is thereby formed by the action of the amino acid binding to the tRNA molecule at the site A and the peptidyl transferase. Finally, the ribosome moves by three nucleotides along the mRNA, and it transfers the peptidyl tRNA newly formed at the site A to the site P.

It is known that aminoglycoside-type antibiotics such as streptomycin and hygromycin specifically reduce the translational proof reading activity of ribosome and induce misreading of mRNA codons. In one embodiment of the invention, the mutation of the ribosomal protein S12 can be obtained by screening the mutants that can grow in the presence of an antibiotic such as streptomycin. As a result, by altering its structure and function in protein translation, the mutant ribosome acquires antibiotic resistance in one aspect, and significant influences on the protein translation efficiency and proof reading activity in another aspect.

In one embodiment of the invention, there is provided a mutant strain that has a mutation of improving the protein translation efficiency in the ribosomal protein S12. The mutation may be of any type that gives resistance to or dependence on streptomycin or any other type that does not give such resistance or dependence, so far as it improves the protein synthesis activity of cell extract. Preferably, it has a substitution at any of lysine 43, arginine 86, valine 87, lysine 88, aspartic acid 89, leucine 90, proline 91, glycine 92 or arginine 94 in the amino acid sequence of SEQ ID NO:2, as attaining a favorable result. For example, lysine 43 may be substituted with any of other 19 types of natural amino acids, but is preferably substituted with a hydrophilic amino acid, more preferably with threonine for attaining high protein synthesis activity. Lysine 88 may also be substituted with any of other 19 types of natural amino acids, but is preferably with a hydrophilic amino acid, more preferably with arginine for providing an advantageous effect. Leucine 90 or arginine 94 substitution does not bring about resistance to streptomycin but may improve protein synthesis activity. The mutation of the ribosomal protein S12 screened in the presence of an antibiotic is generally for single amino acid substitution, but screening with plural antibiotics enables a mutation with two or more amino acid substitutions. Site-specific mutation and homologous recombination to chromosomal DNA, as is described hereunder, brings about the formation of a mutant *E. coli* having a desired amino acid substitution in the ribosomal protein S12.

In another embodiment of the invention, there is provided a mutant of ribosomal protein S12 that has an excellent protein synthesis activity in the stationary phase of *E. coli*. For preparing an *E. coli* S-30 extract, generally employed are cells in a logarithmic growth phase (log phase, exponential phase) having a high protein synthesis activity. The logarithmic growth phase means a phase where the number of bacteria or cells increases logarithmically. When cells are inoculated in a new vessel, they first take a period of time before they could adapt to the new condition (lag phase), and then they grow more and more in the subsequent logarithmic growth phase and the growth of the cells will soon stop depending on the size of the vessel and on the degree of degradation of the culture medium, and thus the cells are in a stationary phase. In general, the cells in the logarithmic growth phase have a higher protein synthesis activity than those in the stationary phase, but they require a larger amount of the culture medium than that in the stationary phase for preparing a predetermined number of cells since the cell concentration is low. Accordingly, if the S-30 extract having a high protein synthesis activity could be prepared from *E. coli* cells in the stationary stage, then it could be an extremely efficient process. One example of the ribosomal protein S12 mutant having a high protein synthesis activity in the stationary phase is a mutant (K88E) having the amino acid sequence of SEQ ID NO:2 where lysine 88 is substituted with glutamic acid. The reason why the S-30 extract from the cells of the stationary-phase K88E mutant could have a higher protein synthesis activity than the wild strain may be presumed as follows: As a result of investigation of the characteristics of the ribosome in the extracts, the ribosome in the stationary-phase cells of the K88E mutant is more stable than those of the parent strain and the protein synthesis activity per unit ribosome of the mutant is higher than that of the parent strain.

Of the E. coli mutants, those capable of growing in the presence of streptomycin may have the possibility that the translational proof reading activity of the ribosome is improved, or that is, the mRNA codon recognition thereof is more accurate. In general, the codon recognition accuracy means the reduction in the affinity for tRNA of the ribosome, and it is thereby believed that a correct tRNA could be more strictly selected from similar tRNAs competitively bonding to the site A of the ribosome. Accordingly, it is believed that the cell extract of the E. coli mutant of the invention is advantageous in that its protein synthesis amount increases due to the improvement in the translation efficiency thereof and its codon recognition accuracy also increases.

(Screening of E. coli Strain Having Mutation at the Ribosomal Protein S12 Gene)

E. coli strains having a mutation at the gene encoding ribosomal protein S12 (rpsL) may be screened in various methods. One method comprises selecting an E. coli mutant capable of growing in the presence of high-concentration streptomycin. The E. coli mutant of the type may be obtained, for example, by plating a suspension of E. coli cells, either directly as it is or after treatment with UV irradiation, to an agar medium that contains from 5 to 100 times the minimal growth inhibitory concentration of streptomycin (50 to 1000 µg/ml) and harvesting the colonies formed within 2 to 7 days. The E. coli strains applicable to the process include E. coli A19 (rna, met), BL21, BL21star, BL21codon plus.

Another method is as follows: An rpsL gene that has a desired amino acid substitution by introducing a site-specific mutation thereinto is constructed, and this is cloned into a plasmid DNA and is introduced into the chromosomal DNA of E. coli through homologous recombination. The rpsL gene of E. coli is already known, and its nucleotide sequence is registered, for example, in the database of GenBank or DDBJ as Acc No. V00355. The nucleotide sequence that corresponds to the coding region is shown in SEQ ID NO:1. A site-specific mutation is introduced into the rpsL gene cloned from the chromosomal DNA of E. coli through PCR, whereby an amino acid substitution mutation may be introduced into the desired site of the ribosomal protein S12. The method of in-vitro introduction of a site-specific mutation into a cloned DNA includes, for example, a Kunkel method (Kunkel, T. A. et al., Methods Enzymol. 154, 367-382 (1987)); a double primer method (Zoller, M. J. and Smith, M., Methods Enzymol. 154, 329-350 (1987)); a cassette mutation method (Wells, et al., Gene 34, 315-323 (1985)); a mega-primer method (Sarkar, G. and Sommer, S. S., Biotechniques 8, 404-407 (1990)). Next, the mutation-introduced DNA fragment is cloned into a plasmid vector for homologous recombination. The vector has, for example, a chloramphenicol-resistant gene as a selective marker. When the plasmid in which the rpsL gene with the site-specific mutation was inserted, is introduced into E. coli having a DNA recombination capability, for example, E. coli BL21, then it results in homologous recombination. The double recombinant with recombination at two sites of the introduced plasmid and the chromosomal DNA is given streptomycin resistance and is susceptible to chloramphenicol The two-stage screening provides an E. coli mutant that has the desired rpsL gene inserted into the chromosomal DNA (e.g., see Hosoya et al. (vide supra)).

(Preparation of an Extract from the Mutant E. coli Cells)

As an E. coli extract, the S-30 extract prepared by the similar method of Zubay, et al. (supra) can be used. The E. coli S-30 extract contains all the enzymes and factors from E. coli necessary for transcription and translation. Additionally, supplemental mixture can be added. A concrete S-30 extract is prepared by first culturing the E. coli and harvesting the cells by centrifugation and the like. The recovered cells are washed and resuspended in the buffer, and then lysed or broken with a French press, glass beads, Waring blender, or the like. The insoluble matter of disrupted E. coli cells is removed by centrifugation and the supernatant is then combined with a pre-incubation mixture and incubated. While this operation degrades the endogenous DNA and RNA, it may further include a step of adding a calcium salt or microccocal nuclease to degrade contaminating nucleic acids. The extract is then dialyzed to remove endogenous amino acids, nucleic acids nucleosides etc., stored in liquid nitrogen or −80° C. after dispensing appropriate aliquots.

For performing a protein synthesis reaction, the S-30 extract is supplemented with all or a portion of the followings: Tris-acetate, dithiothreitol (DTT), the NTPs (ATP, CTP, GTP, and UTP), phosphoenol pyruvate, pyruvate kinase, at least one amino acid (20 naturally occurring amino acids including derivatives thereof. In case of labeling the protein with a radioisotope, rests of a radio-labeled amino acid are added.), polyethylene glycol (PEG), folic acid, cAMP, tRNA, ammonium acetate, potassium acetate, potassium glutamate, an optimized concentration of magnesium acetate, and the like. These supplemental solutions are usually stored separately from the S-30 extract, and then combined just before use. Alternatively, the reaction mixture can be made by combining an S-30 extract and supplemental mix, freezing and thawing the combination to remove the RNA degradsomes (see International Publication WO 01/83805).

In the present invention, an energy regeneration system may preferably be a combination of 0.02 to 5 µg/µl creatine kinase (CK) and 10 to 100 mM creatine phosphate (CP), to which it is not limited, and any known substance may be employed, such as a combination of 1 to 20 mM phosphoenol pyruvate (PEP) and 0.01 to 1 µg/µl pyruvate kinase and the like. Any of PK and CK is an enzyme which regenerates an ATP from an ADP, and requires PEP and CP as respective substrates.

The cell extract or supplemental mix can be distributed as a product easy for use in aliquots. These products can be stored at frozen or dried state, and distributed as a kit in suitable containers for storage and for shipment to users. The kit can be accompanied by an instruction manual, a positive control DNA, a vector DNA and the like.

(Protein Synthesis in Cell-Free Protein Synthesis System)

Protein synthesis in a cell-free protein synthesis system includes a system where transcription and translation are separately effected in different test tubes like that for the nucleus and the cytoplasm of eukaryotic cells, and a transcription/translation coupling system where the two are effected simultaneously. In the method of protein production of the invention, an extract of prokaryotic cells, E. coli is used, and the method is applicable to any of such reaction systems. For the invention, however, the transcription/translation coupling system is preferred in which any unstable mRNA is not directly processed.

First, a polynucleotide that encodes the protein to be expressed is prepared. In the invention, the "protein" may be any of a full-length protein having a biological activity or a polypeptide fragment of a part of such a full-length protein. Many proteins, especially many eukaryotic proteins have plural domain structures as a result of evolution through gene duplication, in which each domain has a structure and a function characteristic of itself. Accordingly, it is extremely effective to express such proteins according to the method of the invention. The nucleic acid that encodes the intended protein may be either DNA or RNA, and it may be extracted from the cells or tissues of eukaryotes or prokaryotes in any known method. DNA cloned from a cDNA library and the like according to a known method is also employable herein.

For in-vitro synthesis of mRNA from a cloned cDNA, for example, employable is a phage-derived transcriptional system such as that from T7, T3 or SP6, or an E. coli-derived transcriptional system. For mRNA synthesis by the use of the system, employable are any commercially-available kits such as MEGAscript (Ambion's trade name) and RiboMAX (Promega's trade name). The distance and the base sequence of the 5'-non-translational region between the translation initiation codon (ATG) and the promoter are important, and the region must include the SD sequence of E. coli. After a desired gene has been inserted into a suitable vector, the plasmid DNA is purified according to an alkali-SDS method or by the use of a DNA-coupling resin. Alternatively, using a primer that contains the promoter, the DNA fragment amplified through PCR may be used as a template. This is an extremely simple and rapid method for simultaneously processing different types of samples. In a transcription/translation coupling system, the plasmid DNA prepared herein or the PCR product can be directly used as the template in the cell-free protein synthesis system.

A semi-batch process where a small-molecule substrate such as ATP, GTP, amino acid or creatine phosphate is supplied to the reaction mixture via a dialytic membrane or an ultrafilter while the waste is removed; and a continuous process where the product is also removed via the membrane are reported. According to these processes, the reaction time may be prolonged by 5 to tens times, and a large quantity of protein can be synthesized. For example, according to a Kigawa et al's process (Kigawa, T., et al., FEBS Letters 1999, 442:15-19) or to the method described in JP-A 2000-175695, the above-mentioned reaction mixture is introduced inside the space of a dialytic membrane that has a molecular cutoff level of at least 10,000, preferably at least 50,000, and this is dialyzed against a dialytic external liquid (including amino acid, energy source) of from 5 to 10 volume times the reaction mixture. The dialysis is carried out generally at 20 to 40° C., preferably at 23 to 30° C. with stirring, and at the time when the reaction speed is lowered, the dialytic external liquid is exchanged with a fresh one. The producibility in the optimized cell-free protein synthesis system is far higher than that in an intracellular system as in E. coli cells.

EXAMPLES

The invention is described more concretely in the following Examples. In the Examples, an E. coli strain BL21 was used as a parent strain, and the colonies having grown in the presence of streptomycin were screened to give 9 mutants. These mutants were analyzed for their properties such as protein synthesis activity.

Example 1

Mutation from E. coli BL21

Mutants from a parent strain, E. coli BL21 were screened for those capable of growing in the presence of streptomycin. 150 streptomycin-resistant spontaneous mutants of E. coli BL21 were obtained, and these were sequenced for the full-length rpsL gene. As a result, it was confirmed that about 80% of the resistant mutants have a mutation in the rpsL gene. Nine such rpsL mutants were obtained, and their typical strains are shown in Table 1. In Table 1, SmR in the phenotype column means streptomycin resistance; and SmD means streptomycin dependence. The mutation site indicates the base substitution site in the nucleotide sequence shown in SEQ ID NO:1; and the amino acid substitution indicates the amino acid substitution site in the amino acid sequence shown in SEQ ID NO:2. The symbol for the base and the amino acid is a one-letter abbreviation.

TABLE 1

List of Mutants from E. coli BL21

| Strain (Mutant) | Mutation Site | Amino Acid Substitution | Phenotype |
| --- | --- | --- | --- |
| BL21 | — | — | wild type |
| KO-365 | A128G | K43R | SmR |
| KO-368 | A129C | K43N | SmR |
| KO-371 | A128C | K43T | SmR |
| KO-374 | A128T | K43I | SmR |
| KO-375 | A263G | K88R | SmR |
| KO-376 | C272T | P91L | SmR |
| KO-378 | C272A | P91Q | SmR |
| KO-430 | A262G | K88E | SmR |
| KO-431 | G275A | G92D | SmD |

Example 2

Cultivation in the Presence of Antibiotic

Growth curves of E. coli mutant strains (K43T, K43R and K88R) obtained in Example 1 and the parent strain (wild-type BL21) cultivated in 2×YT medium at 37° C. were shown in FIG. 1, respectively In FIG. 1, the turbidity (600 nm absorbance) of the cultures sampled within a period of from 2 hours to 9 hours after the start of the cultivation was measured, and used to estimate the amount of cells. Any of the mutant strains shown in FIG. 1, showed the almost same growth pattern as that of wild-type, whereas the amount of cells of the mutant K43T was the largest in 8 hours after the start of the cultivation.

Example 3

Preparation of Cell Extract from E. coli Mutants, and Comparison of Protein Synthesis Activity by Cat Assay The mutant strains shown in Table 1 were separately cultivated in 2×YT medium (16 g/liter of bactotrypsin, 10 g/liter of yeast extract, and 5 g/liter of NaCl) at 37° C., and the cells in the mid-log phase ($OD_{600}$=3, about $10^9$ cells/ml) were collected. According to the method of Zubay et al. (vide supra), an *E. coli* extract S-30 was prepared from these cells. Protein synthesis was carried out as follows: To a solution having the composition shown in the following Table 2, added was 120 ng of pK7-CAT (CAT expression vector; see Kim et al., Eur. J. Biochem. 239, 881-886, 1996). 7.2 μl of the *E. coli* S-30 extract was added to it to make 30 μl as a whole. The reaction solution was batchwise incubated at 37° C. for 1 hour. Thus synthesized, the CAT protein was quantified according to the method of Shaw et al. (see Methods Enzymol., 735-755, 1975). The results are shown in FIG. 2.

TABLE 2

| Ingredients | Concentration |
| --- | --- |
| HEPES-KOH pH 7.5 | 58.0 mM |
| Dithiothreitol | 2.3 mM |
| ATP | 1.2 mM |
| CTP, GTP, UTP | 0.9 mM each |
| Creatine phosphate | 81.0 mM |
| Creatine kinase | 250.0 μg/ml |
| Polyethylene glycol 8000 | 4.00% |
| 3',5'-cAMP | 0.64 mM |
| L(-)-5-Formyl-5,6,7,8-tetrahydrofolic acid | 35.0 μg/ml |
| *E. coli* total tRNA | 170.0 μg/ml |
| Potassium glutamate | 200.0 mM |
| Ammonium acetate | 27.7 mM |
| Magnesium acetate | 10.7 mM |
| Amino acids (20 types) | 1.0 mM each |
| T7RNA polymerase | 16.0 units/μl |

Figure 2:
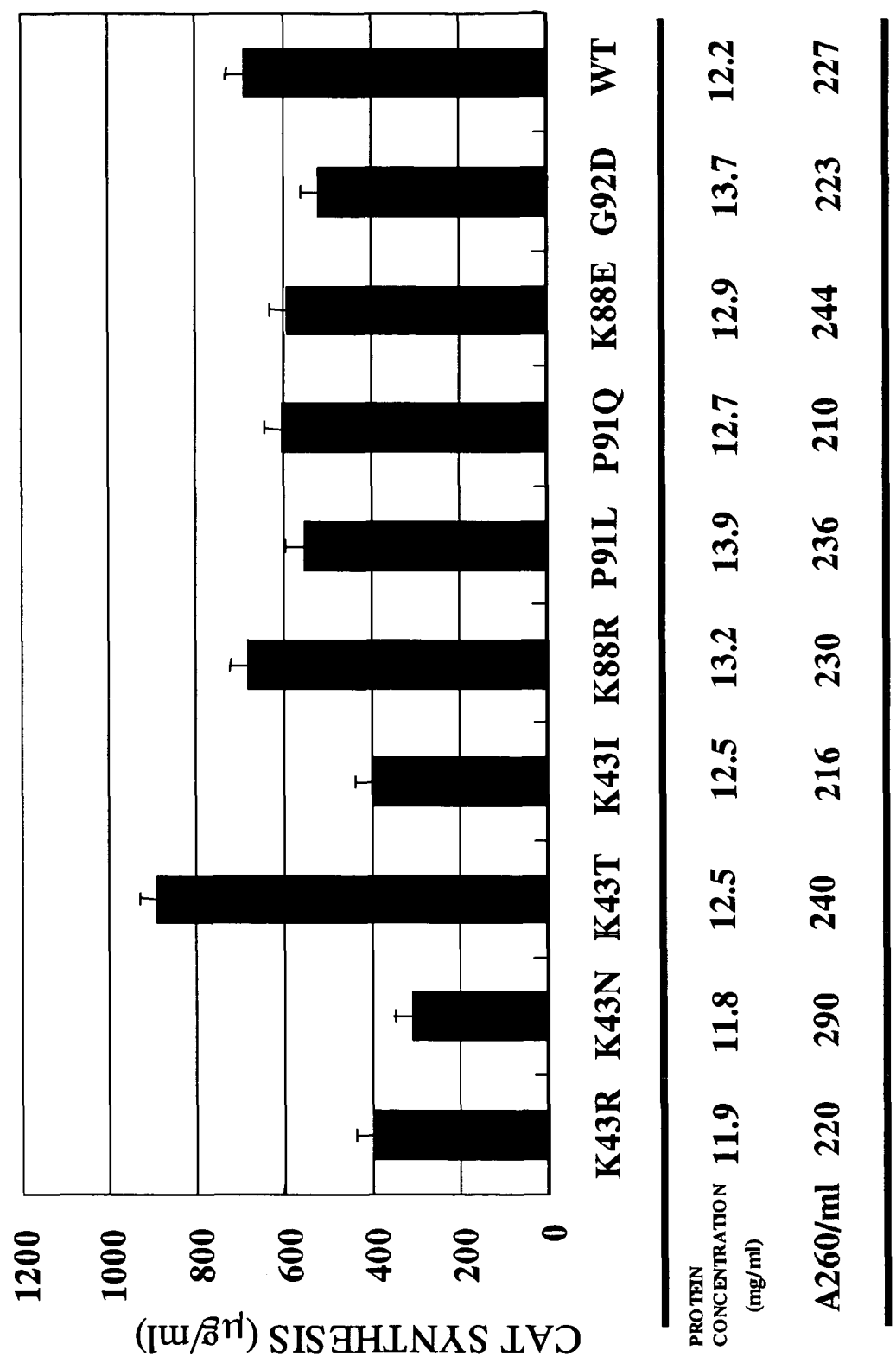
FIG. 2 shows the results of CAT synthesis by the use of an extract of wild-type *E. coli* and that of *E. coli* having a mutation in the ribosomal protein S12. CAT synthesis was carried out according to a batch process at 37° C. for 1 hour.

As in FIG. 2, it is understood that the amino acid substitution at position 43 of the ribosomal protein S12 has a significant influence on the protein synthesis activity. In particular, the protein synthesis activity of the K43T mutant was about 1.3 times that of the wild type (WT) BL21. In the Table below FIG. 2, shown are the data of the protein concentration of the extract from each *E. coli* strain and the 260 nm absorbance thereof (this essentially indicates the nucleic acid concentration of the extract). From the data, it is understood that there is no direct relationship between the variations in the protein amount and the nucleic acid amount in each extract and the protein synthesis activity of the extract.

Example 4

Characteristic Evaluation of Various *E. coli* Mutant Strains

Figure 3:
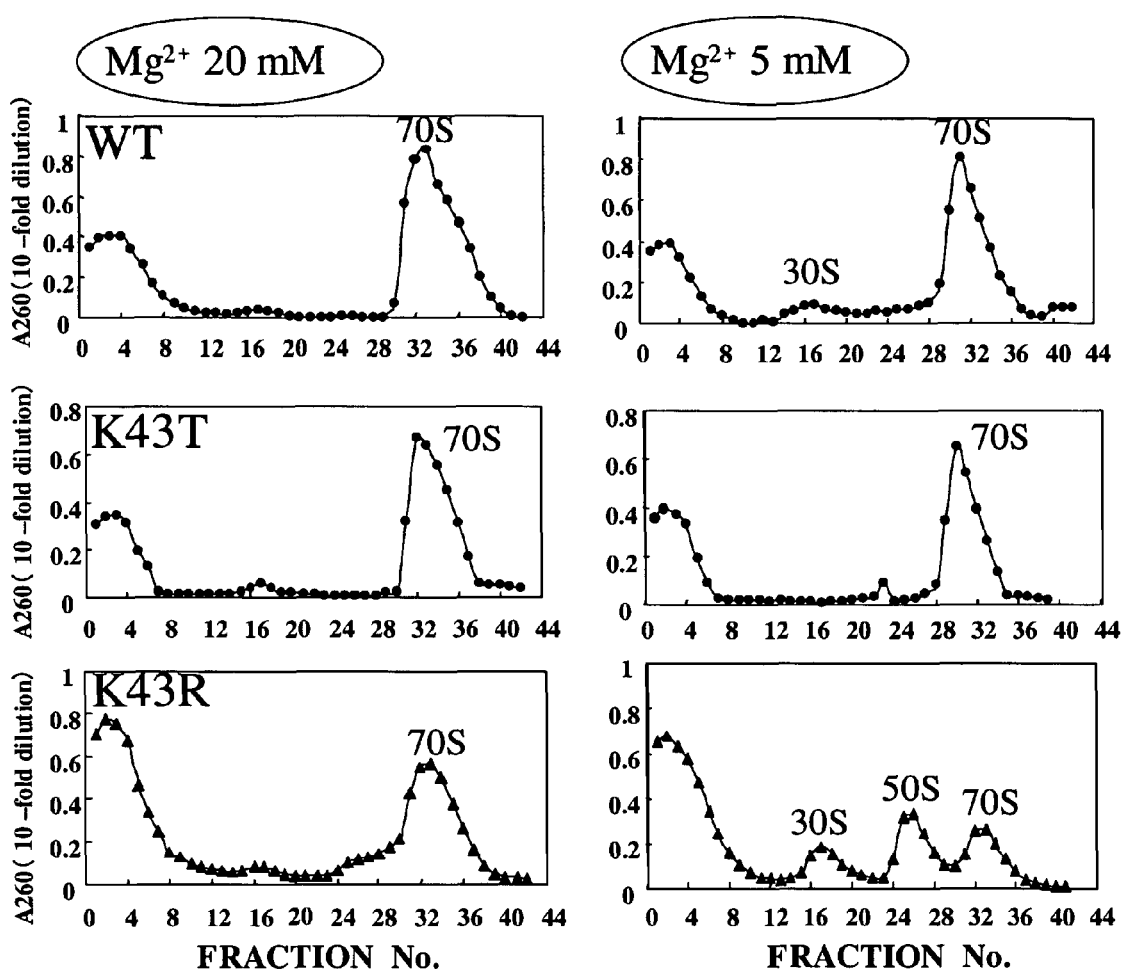
FIG. 3 shows the results of analysis through sucrose density gradient ultracentrifugation of S-30 extract of wild-type *E. coli* and *E. coli* having amutation in the ribosomal protein S12 in the presence of $Mg^{2+}$ of a different concentration.

At a fixed $Mg^{2+}$ concentration of 20 mM or 5 mM, an S-30 extract was prepared from wild-type *E. coli* and *E. coli* mutants (K43T, K43R) in the same manner as in Example 3. The extract was put on a buffer (20 mM HEPES, 20 mM or 5 mM $MgCl_2$, 100 mM $NH_4Cl$, 4.5 mM 2-mercaptoethanol) containing from 6 to 38% of sucrose gradient, and centrifuged at 17000 rpm for 17 hours by the use of a Beckman SW28 rotor. Then, this was divided into fractions of 0.8 ml each. In FIG. 3, the vertical axis indicates an estimated value of the ribosome-existing fraction through presumption of the 260 nm absorbance of the sample. As in FIG. 3, it is understood that, in the wild-type *E. coli*, a part of the 70S ribosome dissociated to give a 30S subunit at the low $Mg^{2+}$ concentration of 5 mM. This is remarkable in the K43R mutant, in which a large part of the 70S ribosome dissociated into subunits 50S and 30S at the low $Mg^{2+}$ concentration of 5 mM. As opposed to this, the K43T mutant showed little dissociation of the 70S ribosome even at the low $Mg^{2+}$ concentration. These results suggest that the K43T mutation in the ribosomal protein S12 may stabilize the total ribosomal structure.

Example 5

Protein Synthesis from Various Mouse cDNAs

Using various mouse cDNAs as templates, protein synthesis was carried out in an S-30 extract from wild-type and K43T mutant *E. coli*, in which the protein synthesis activity was evaluated. Three clones obtained from a mouse cDNA library (DDBJ Accession Nos. AK003622, AK010399 and AK019487) were used as templates. According to the two-step polymerase chain reaction (2-step PCR), a DNA fragment was prepared by adding a T7 promoter, an SD sequence and a T7 terminator to the cDNA. First, the first PCR was carried out using the primer pair of the nucleotide sequence shown in Table 3.

TABLE 3

| Clone Code | Template cDNA (Acc. No.) | NUcleotide Sequence in forward direction primer (5' → 3') | | Nucleotide Sequence in reverse direction primer (5' → 3') | |
| --- | --- | --- | --- | --- | --- |
| A | AK003622 | CCAGCGGCTCCTCGGGAATGGAACCTTCTCTCTACA | (SEQ ID NO:3) | CCTGACGAGGGCCCCGAGTCATCAGTCCTAAAATTCAC | (SEQ ID NO:4) |
| B | AK010399 | CCAGCGGCTCCTCGGGAATGTTCCCAGAACAGCAG | (SEQ ID NO:5) | CCTGACGAGGGCCCCGAATTCATTAAAGCAAACTTGTGAA | (SEQ ID NO:6) |
| C | AK019487 | CCAGCGGCTCCTCGGGAGAGTACAAAGCGGGAGA | (SEQ ID NO:7) | CCTGACGAGGGCCCCGAATTTTCAATTTCCCATAATCCTT | (SEQ ID NO:8) |

Each primer concentration was 0.25 μm. After the addition of DNA polymerase (by Rosh), 10 cycles at 94° C. for 30 seconds, at 60° C. for 30 seconds and at 72° C. for 2 minutes each; 20 cycles at 94° C. for 30 seconds, at 60° C. for 30 seconds, at 72° C. for 2 minutes plus 5 seconds in every cycle; and finally one cycle at 72° C. for 7 minutes were carried out.

Next, using the first PCR product obtained in the above reaction, a 5'-primer having a histidine tag sequence downstream the T7 promoter sequence:

(T7P-DM5-KH6, SEQ ID NO: 9)
5'-GCTCTTGTCATTGTGCTTCGCATGATTACGAATTCAGATCTCGATCC

CGCGAAATTAATACGACTCACTATAGGGAGACCACAACGGTTTCCCTCTA

GAAATAATTTTGTTTAACTTTAAGAAGGAGATATACATATGAAAGGCAGC

AGCCATCATCATCATCATCACGATTACGATATCCCAACGACCGAAAACCT

CTGTATTTTCAGGGATCCAGCGGCTCCTCGGG-3', the 3'-primer having a T7 terminator sequence:

```
                                              (T7T-DM3-Term, SEQ ID NO: 10)
5'-CGGGGCCCTCGTCAGGATAATAATTGATTGATGCTGAGTTGGCTGCT

GCCACCGCTGAGCAATAACTAGCATAACCCCTTGGGGCCTCTAAACGGGT

CTTGAGGGGTTTTTTGCTGAAAGGAGGAACTATATCCGGATAACCTCGAG

CTGCAGGCATGCAAGCTTGGCGAAGCACAATGACAAGAGC-3',
``` and a universal primer:

```
5'-GCTCTTGTCATTGTGCTTCG-3',    (SEQ ID NO: 11)
``` second PCR was carried out. The concentration of the 5'-primer and the 3-primer in the second PCR solution was 0.05 µM each, and the concentration of the universal primer therein was 1 µM. The amplification condition for the second PCR was the same as that for the first PCR. Next, the resulting DNA fragments were cloned into pPCR2.1 by the use of TOPO TA-cloning kit (by Invitrogen) to thereby construct expression vectors (clone A: P011114-10, clone B: P020107-17, clone C: P020408-01).

In the same manner as in Example 3, each expression vector of the clones A to C was added to 30 µl of the reaction solution shown in Table 2 in the concentration as indicated in Table 4, and batchwise processed at 37° C. for 1 hour for protein synthesis therein. After the reaction, this was roughly purified with Ni-NTA agarose beads, and then subjected to SDS-PAGE, and the protein was stained with a fluorescent dye SYPRO Orange protein gel stains (by Molecular Probes). The band corresponding to the molecular weight of the synthesized protein was detected with a luminoimage analyzer LAS-1000 (by Fuji Photo Film), and quantified. Thus determined, the amount of the three proteins produced in the extract of the mutant K43T was compared with that produced in the wile type, and the data are given in Table 4. It is understood that the amount of the protein expressed by any of the clones A, B and C in the extract from the mutant K43T was larger by 1.5 to 2 times or more, than that expressed in the extract from the wild-type E. coli.

TABLE 4

Comparison of Synthesis Activity with Various Mouse cDNA

| Clone Code | Expression Vector Concentration in Synthesis Reaction Solution | Molecular Weight of Synthesized Protein | Ratio of Protein Production Amount |
|---|---|---|---|
| A | 1 ng/µl | 20726 | 1.58 |
| B | 2.3 ng/µl | 22291 | 2 |
| C | 1 ng/µl | 13549 | 2.2 |

Example 6

Figure 4:
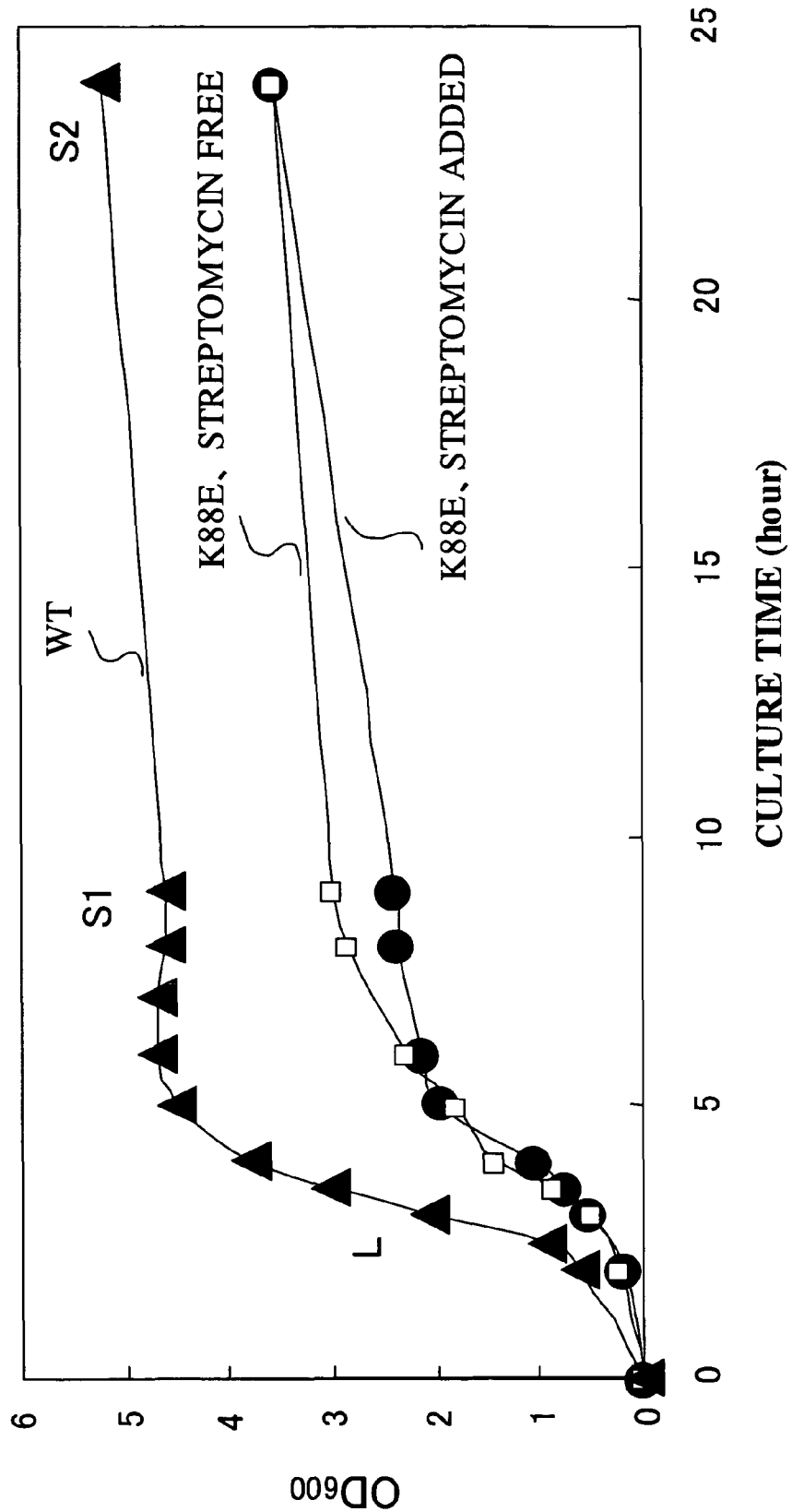
FIG. 4 shows growth curves of wild-type *E. coli* and *E. coli* having K88E-mutation in the ribosomal protein S12, in terms of the culture turbidity ($OD_{600}$) relative to the culture time.

Mutant and wild-type (BL21) cells of E. coli in the mid-log phase (L phase), stationary phase 1 (S1 phase) and stationary phase 2 (S2 phase) obtained in Example 1 were used to prepare cell-free extracts, and these were analyzed in point of their protein synthesis activity. Using an ordinary liquid medium, the cells were cultivated to prepare seed cultures. The seed culture was inoculated into 7 liters of 2×YT medium in a fermentor, and incubated therein with full aeration with stirring at 400 rpm at 37° C. This was periodically sampled out for 24 hours after the start of the incubation, and the turbidity of each sample (as 600 nm absorbance) was measured, from which the amount of the cells was estimated. As a result, it is understood that the growing speed of the K88E mutant was significantly lower than that of the wild-type E. coli, as in FIG. 4. In FIG. 4, the growth curves of the K88E mutant cultivated with or without streptomycin added thereto are shown. In both cases, the growing speed of the mutant cells was significantly low, and the amount of the mutant cells having grown within 24 hours is about a half of that the wild-type cells. The other mutants gave nearly the same growth curve as that of the wild-type strain.

Figure 5:
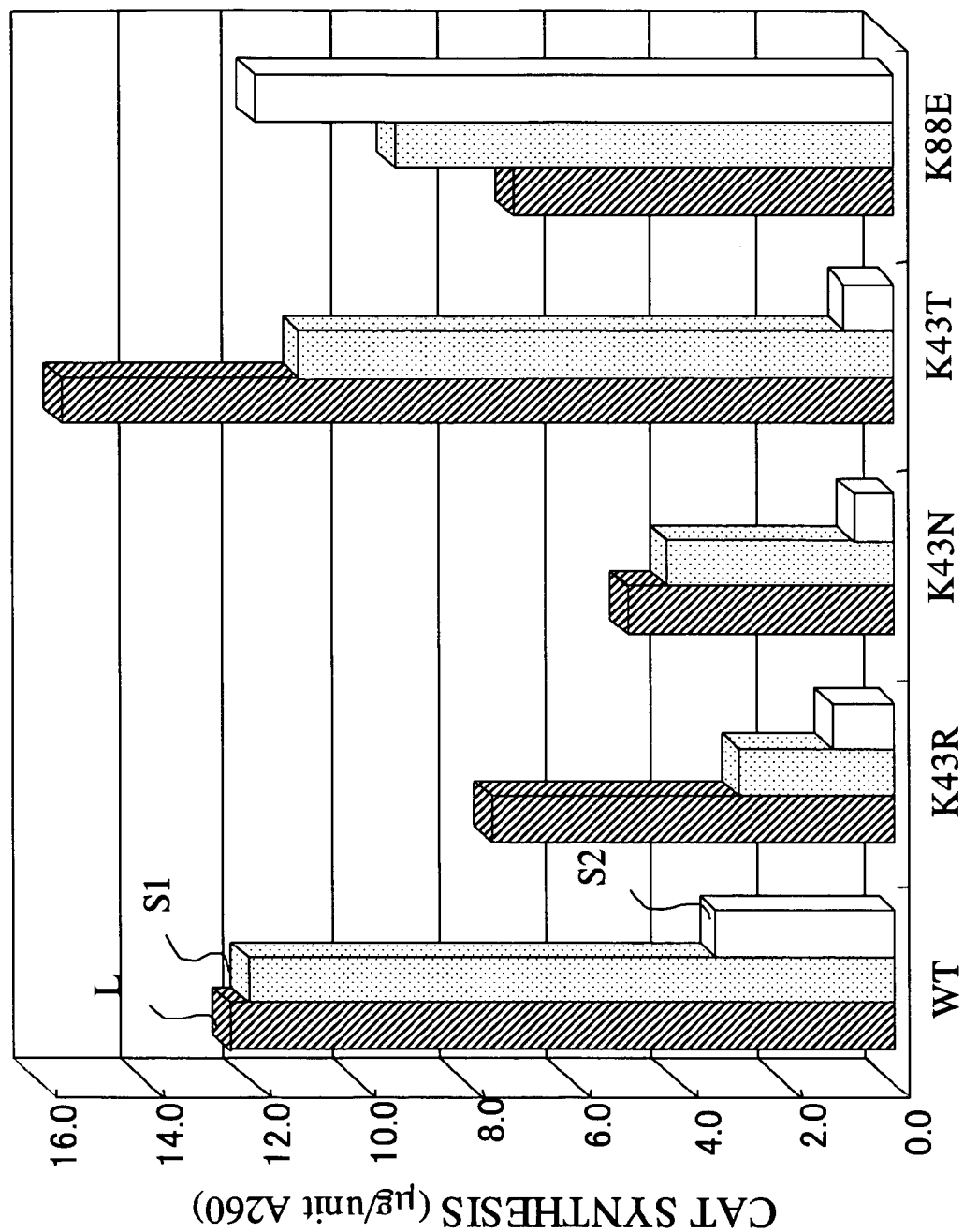
FIG. 5 shows the results of CAT synthesis by the use of S-30 extract prepared from the cells of wild-type *E. coli* and that from the cells of *E. coli* having a mutation in the ribosomal protein S12 in different growth stages (L, S1 and S2)

The mid-log phase (L phase) of the K43R, K43N and K43T mutants and the wild-type strain (WT) was at OD600=3; and that of the K88E mutant is after 6 hours from the start of cultivation. The S1 phase of all the strains is after 9 hours from the start of cultivation; and the S2 phase thereof is after 24 hours from the start of cultivation. The cells in these phases were collected, and an E. coli S-30 extract was prepared from these in the same manner as in Example 3, and the CAT protein mass was determined. The 260 nm absorbance of the S-30 extract was measured, and the amount of crude ribosome was obtained, and the CAT synthesis amount per unit ribosome is shown in FIG. 5. From the results in FIG. 5, it is understood that the CAT synthesis activity of the S-30 extract prepared from the L-phase cells of the K43T mutant was the highest, and the CAT synthesis activity of the S-30 extract prepared from the S2-phase cells of the K88E mutant was the highest. In FIG. 5, the vertical axis indicates the value obtained by dividing the CAT synthesis amount (µg) by the 260 nm absorbance (A260) for the crude ribosome amount in the S-30 extract.

INDUSTRIAL APPLICABILITY

The cell extract prepared from the E. coli mutant of the invention has a specific mutation at the ribosomal protein S12, and as compared with that from wild-type E. coli cells, it shows a significantly higher protein synthesis activity.

There is a possibility that the ribosomal protein S12 mutant may have an influence on the codon reading efficiency of mRNA in the translation stage, and therefore there is a probability that the mutant may have the ability to noticeably increase the expression efficiency of mRNA of which the production amount was small in a conventional method. In particular, of the E. coli mutants of the invention, those capable of growing in the presence of streptomycin may readily prevent their culture from being contaminated with any other external cells, and an extract for cell-free protein synthesis can be efficiently prepared from them.

The invention claimed is:

1. A method for increasing the yield of a protein synthesized in vitro comprising:
   expressing a polynucleotide encoding said protein using a composition comprising an S30 extract for cell-free protein synthesis, which S30 extract is prepared from *Esherichia coli* having a mutation in the ribosomal protein S12 gene encoding a SEQ ID NO: 2 variant that substitutes threonine for the lysine amino acid residue at position 43 of the amino acid sequence represented in SEQ ID No:2, whereby the yield of protein obtained is increased compared to the yield obtained using an S30 extract prepared from wild type *Esherichia coli*.

2. A method for producing a protein in vitro comprising:
   expressing a polynucleotide encoding said protein using a composition comprising an S30 extract for cell-free protein synthesis, which S30 extract is prepared from *Esherichia coli* having a mutation in the ribosomal protein S12 gene encoding a SEQ ID NO: 2 variant that substitutes threonine for the lysine amino acid residue at position 43 of the amino acid sequence represented in SEQ ID No:2, whereby the yield of protein obtained is increased compared to the yield obtained using an S30 extract prepared from wild type *Esherichia coli*.

3. The method of claim 2, wherein the yield of the protein is from 1.5 to 2 times that of such an S30 extract prepared from wild type *Eshericia coli*.

4. The method of claim 2, wherein the *Eshericia coli* are collected at mid-log phase of culture for preparation of said S30 extract.

* * * * *

SEQUENCE LISTING

<160> NUMBER OF SEQ ID NOS: 11

<210> SEQ ID NO 1
<211> LENGTH: 375
<212> TYPE: DNA
<213> ORGANISM: Escherichia coli
<220> FEATURE:
<221> NAME/KEY: CDS
<222> LOCATION: (1)..(375)

<400> SEQUENCE: 1

```
atg gca aca gtt aac cag ctg gta cgc aaa cca cgt gct cgc aaa gtt      48
Met Ala Thr Val Asn Gln Leu Val Arg Lys Pro Arg Ala Arg Lys Val
1               5                   10                  15 gcg aaa agc aac gtg cct gcg ctg gaa gca tgc ccg caa aaa cgt ggc      96
Ala Lys Ser Asn Val Pro Ala Leu Glu Ala Cys Pro Gln Lys Arg Gly
            20                  25                  30 gta tgt act cgt gta tat act acc act cct aaa aaa ccg aac tcc gcg    144
Val Cys Thr Arg Val Tyr Thr Thr Thr Pro Lys Lys Pro Asn Ser Ala
        35                  40                  45 ctg cgt aaa gta tgc cgt gtt cgt ctg act aac ggt ttc gaa gtg act    192
Leu Arg Lys Val Cys Arg Val Arg Leu Thr Asn Gly Phe Glu Val Thr
    50                  55                  60 tcc tac atc ggt ggt gaa ggt cac aac ctg cag gag cac tcc gtg atc    240
Ser Tyr Ile Gly Gly Glu Gly His Asn Leu Gln Glu His Ser Val Ile
65                  70                  75                  80 ctg atc cgt ggc ggt cgt gtt aaa gac ctc ccg ggt gtt cgt tac cac    288
Leu Ile Arg Gly Gly Arg Val Lys Asp Leu Pro Gly Val Arg Tyr His
                85                  90                  95 acc gta cgt ggt gcg ctt gac tgc tcc ggc gtt aaa gac cgt aag cag    336
Thr Val Arg Gly Ala Leu Asp Cys Ser Gly Val Lys Asp Arg Lys Gln
            100                 105                 110 gct cgt tcc aag tat ggc gtg aag cgt cct aag gct taa                375
Ala Arg Ser Lys Tyr Gly Val Lys Arg Pro Lys Ala
        115                 120
```

<210> SEQ ID NO 2
<211> LENGTH: 124
<212> TYPE: PRT
<213> ORGANISM: Escherichia coli

<400> SEQUENCE: 2

```
Met Ala Thr Val Asn Gln Leu Val Arg Lys Pro Arg Ala Arg Lys Val
1               5                   10                  15

Ala Lys Ser Asn Val Pro Ala Leu Glu Ala Cys Pro Gln Lys Arg Gly
            20                  25                  30

Val Cys Thr Arg Val Tyr Thr Thr Thr Pro Lys Lys Pro Asn Ser Ala
        35                  40                  45

Leu Arg Lys Val Cys Arg Val Arg Leu Thr Asn Gly Phe Glu Val Thr
    50                  55                  60

Ser Tyr Ile Gly Gly Glu Gly His Asn Leu Gln Glu His Ser Val Ile
65                  70                  75                  80

Leu Ile Arg Gly Gly Arg Val Lys Asp Leu Pro Gly Val Arg Tyr His
                85                  90                  95

Thr Val Arg Gly Ala Leu Asp Cys Ser Gly Val Lys Asp Arg Lys Gln
            100                 105                 110

Ala Arg Ser Lys Tyr Gly Val Lys Arg Pro Lys Ala
        115                 120
```

```
<210> SEQ ID NO 3
<211> LENGTH: 36
<212> TYPE: DNA
<213> ORGANISM: Artificial Sequence
<220> FEATURE:
<223> OTHER INFORMATION: Synthetic forward primer for clone A

<400> SEQUENCE: 3
ccagcggctc ctcgggaatg gaaccttctc tctaca                            36

<210> SEQ ID NO 4
<211> LENGTH: 38
<212> TYPE: DNA
<213> ORGANISM: Artificial Sequence
<220> FEATURE:
<223> OTHER INFORMATION: Synthetic reverse primer for clone A

<400> SEQUENCE: 4
cctgacgagg gccccgagtc atcagtccta aaattcac                          38

<210> SEQ ID NO 5
<211> LENGTH: 35
<212> TYPE: DNA
<213> ORGANISM: Artificial Sequence
<220> FEATURE:
<223> OTHER INFORMATION: Synthetic forward primer for clone B

<400> SEQUENCE: 5
ccagcggctc ctcgggaatg ttcccagaac agcag                             35

<210> SEQ ID NO 6
<211> LENGTH: 40
<212> TYPE: DNA
<213> ORGANISM: Artificial Sequence
<220> FEATURE:
<223> OTHER INFORMATION: Synthetic reverse primer for clone B

<400> SEQUENCE: 6
cctgacgagg gccccgaatt cattaaagca aacttgtgaa                        40

<210> SEQ ID NO 7
<211> LENGTH: 34
<212> TYPE: DNA
<213> ORGANISM: Artificial Sequence
<220> FEATURE:
<223> OTHER INFORMATION: Synthetic forward primer for clone C

<400> SEQUENCE: 7
ccagcggctc ctcgggagag tacaaagcgg gaga                              34

<210> SEQ ID NO 8
<211> LENGTH: 40
<212> TYPE: DNA
<213> ORGANISM: Artificial Sequence
<220> FEATURE:
<223> OTHER INFORMATION: Synthetic reverse primer for clone C

<400> SEQUENCE: 8
cctgacgagg gccccgaatt ttcaatttcc cataatcctt                        40

<210> SEQ ID NO 9
<211> LENGTH: 227
<212> TYPE: DNA
<213> ORGANISM: Artificial Sequence
<220> FEATURE:
<223> OTHER INFORMATION: Synthetic 5' primer

<400> SEQUENCE: 9
```

```
gctcttgtca ttgtgcttcg catgattacg aattcagatc tcgatcccgc gaaattaata      60
cgactcacta tagggagacc acaacggttt ccctctagaa ataattttgt ttaactttaa     120
gaaggagata tacatatgaa aggcagcagc catcatcatc atcatcacga ttacgatatc     180
ccaacgaccg aaaacctgta ttttcaggga tccagcggct cctcggg                   227

<210> SEQ ID NO 10
<211> LENGTH: 187
<212> TYPE: DNA
<213> ORGANISM: Artificial Sequence
<220> FEATURE:
<223> OTHER INFORMATION: Synthetic 3' primer

<400> SEQUENCE: 10
cggggccctc gtcaggataa taattgattg atgctgagtt ggctgctgcc accgctgagc      60
aataactagc ataacccctt ggggcctcta aacgggtctt gaggggtttt ttgctgaaag     120
gaggaactat atccggataa cctcgagctg caggcatgca agcttggcga agcacaatga     180
caagagc                                                              187

<210> SEQ ID NO 11
<211> LENGTH: 20
<212> TYPE: DNA
<213> ORGANISM: Artificial Sequence
<220> FEATURE:
<223> OTHER INFORMATION: Synthetic universal primer

<400> SEQUENCE: 11
gctcttgtca ttgtgcttcg                                                  20
```